(12) United States Patent
Baba et al.

(10) Patent No.: US 8,905,931 B2
(45) Date of Patent: Dec. 9, 2014

(54) SUBJECT INFORMATION PROCESSING APPARATUS

(75) Inventors: Yoshitaka Baba, Tokyo (JP); Kenichi Nagae, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 493 days.

(21) Appl. No.: 13/027,361

(22) Filed: Feb. 15, 2011

(65) Prior Publication Data

US 2011/0208035 A1    Aug. 25, 2011

(30) Foreign Application Priority Data

Feb. 23, 2010 (JP) ................. 2010-037024

(51) Int. Cl.
A61B 8/00    (2006.01)
A61B 5/00    (2006.01)

(52) U.S. Cl.
CPC .............. *A61B 5/0059* (2013.01); *A61B 8/56* (2013.01); *A61B 8/4483* (2013.01); *A61B 8/4444* (2013.01); *A61B 5/0095* (2013.01)
USPC .............. 600/437; 600/407; 600/476; 367/7

(58) Field of Classification Search
None
See application file for complete search history.

(56) References Cited

U.S. PATENT DOCUMENTS

| | | | | |
|---|---|---|---|---|
| 4,570,638 A | * | 2/1986 | Stoddart et al. | 600/476 |
| 5,349,961 A | * | 9/1994 | Stoddart et al. | 600/476 |
| 5,718,226 A | * | 2/1998 | Riza | 600/437 |
| 6,544,193 B2 | * | 4/2003 | Abreu | 600/558 |
| 6,709,393 B2 | * | 3/2004 | Ogawa | 600/443 |
| 6,979,292 B2 | * | 12/2005 | Kanayama et al. | 600/437 |
| 7,041,063 B2 | * | 5/2006 | Abreu | 600/549 |
| 7,403,805 B2 | * | 7/2008 | Abreu | 600/318 |
| 7,654,957 B2 | * | 2/2010 | Abreu | 600/399 |
| 7,756,559 B2 | * | 7/2010 | Abreu | 600/318 |
| 7,809,417 B2 | * | 10/2010 | Abreu | 600/318 |
| 2002/0049389 A1 | * | 4/2002 | Abreu | 600/558 |
| 2003/0139687 A1 | * | 7/2003 | Abreu | 600/558 |
| 2004/0039297 A1 | * | 2/2004 | Abreu | 600/558 |
| 2004/0039298 A1 | * | 2/2004 | Abreu | 600/558 |
| 2005/0004458 A1 | * | 1/2005 | Kanayama et al. | 600/437 |
| 2005/0187471 A1 | * | 8/2005 | Kanayama et al. | 600/437 |
| 2007/0016074 A1 | * | 1/2007 | Abreu | 600/475 |
| 2007/0142718 A1 | * | 6/2007 | Abreu | 600/323 |
| 2008/0306371 A1 | * | 12/2008 | Fukutani et al. | 600/407 |
| 2009/0005685 A1 | * | 1/2009 | Nagae et al. | 600/459 |
| 2009/0036761 A1 | * | 2/2009 | Abreu | 600/318 |

(Continued)

FOREIGN PATENT DOCUMENTS

| | | |
|---|---|---|
| JP | 2005-021380 | 1/2005 |
| JP | 2005-052342 | 3/2005 |

*Primary Examiner* — Nicholas Evoy

(74) *Attorney, Agent, or Firm* — Fitzpatrick, Cella, Harper & Scinto

(57) ABSTRACT

Generally, a photoacoustic signal has a wavelength longer than a general ultrasonic signal. That is, it does not matter even if at the time of acquisition of the photoacoustic signal, an element pitch of a probe is several times as large as at the time of acquisition of the ultrasonic signal. Thus, at the time of acquisition of the photoacoustic signal, a plurality of neighboring elements in a receiving element array are collectively considered as one element, and a phasing process is performed. As a result, the same effect as a plurality of phasing addition circuits are disposed in parallel is obtained, and not only a phasing addition process of the photoacoustic signal but also image reconstruction can be performed in real time at a high speed.

8 Claims, 9 Drawing Sheets

(56) References Cited

U.S. PATENT DOCUMENTS

| | | | |
|---|---|---|---|
| 2009/0275837 A1* | 11/2009 | Shiina et al. | 600/459 |
| 2009/0299185 A1* | 12/2009 | Oikawa et al. | 600/447 |
| 2010/0145180 A1* | 6/2010 | Abreu | 600/399 |
| 2010/0191109 A1* | 7/2010 | Fukutani et al. | 600/437 |
| 2011/0040161 A1* | 2/2011 | Abreu | 600/321 |
| 2011/0066023 A1* | 3/2011 | Kanayama et al. | 600/407 |
| 2011/0083511 A1* | 4/2011 | Taki et al. | 73/602 |
| 2011/0098550 A1* | 4/2011 | Yoda | 600/407 |
| 2011/0128816 A1* | 6/2011 | Baba et al. | 367/11 |
| 2011/0208035 A1* | 8/2011 | Baba et al. | 600/407 |
| 2011/0307181 A1* | 12/2011 | Nagae | 702/19 |
| 2012/0044785 A1* | 2/2012 | Yoda et al. | 367/92 |

* cited by examiner

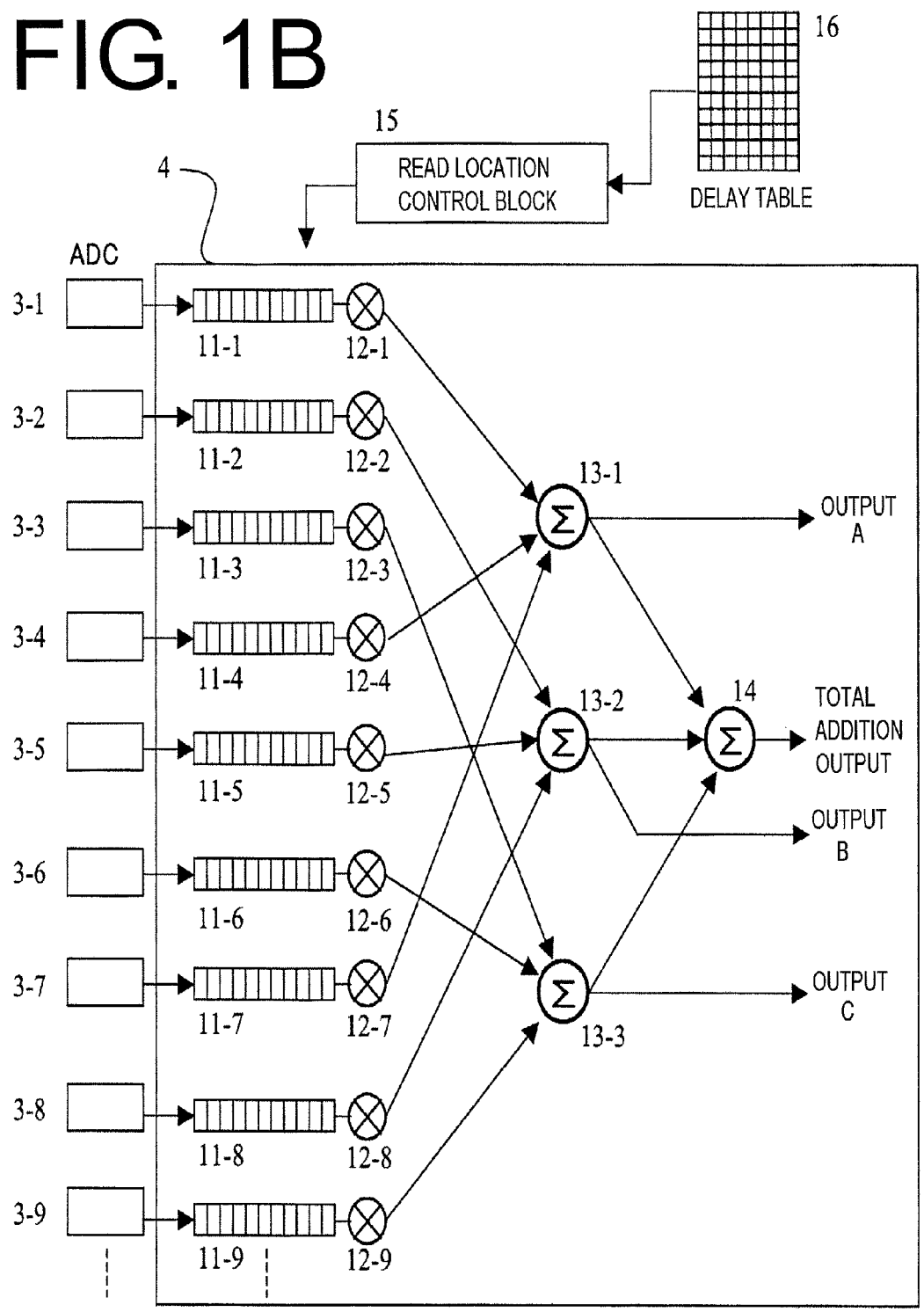

SUBJECT INFORMATION PROCESSING APPARATUS

BACKGROUND OF THE INVENTION

1. Field of the Invention

The present invention relates to a subject information processing apparatus that uses a photoacoustic tomography and an ultrasonic wave echo.

2. Description of the Related Art

From the past, there has been known a photoacoustic effect in which if an electromagnetic wave is irradiated onto a biological object, a photoacoustic wave is generated from the biological object due to a temperature increase and thermal expansion of body tissues of the biological object that are attributable to electromagnetic wave absorption. The photoacoustic wave is a typical ultrasonic wave, but in the following description, an ultrasonic wave generated due to the photoacoustic effect is referred to, particularly, as a photoacoustic wave or a photoacoustic signal. Meanwhile, an ultrasonic wave generated by an ultrasonic wave echo is referred to simply as an ultrasonic wave or an ultrasonic signal for discrimination. A technique called a photoacoustic tomography (PAT) has recently been spotlighted which makes the inside of the biological object visible in a noninvasive manner. There is also an attempt to apply this technique to clinical practice. Further, it is expected that a degree of accuracy of diagnosis will be greatly improved in clinical practice by combining a photoacoustic image obtained in real time with an ultrasonic image obtained by a general ultrasonic wave echo technique.

In a photoacoustic tomography device, light is irradiated onto a target subject, and a photoacoustic wave generated thereby is received by a probe that includes a one-dimensional or two-dimensional receiving element array in which a plurality of receiving elements are disposed. As the receiving element array, one similar to a probe typically used in an ultrasonic wave echo device is widely used. Further, in image reconstruction of the photoacoustic tomography, an attempt to apply various algorithms has been made, but a technique called phasing addition generally used in image data generation of the ultrasonic wave echo device can also be applied. Therefore, an attempt to combine the photoacoustic tomography device with the ultrasonic wave echo device, share a signal processor and an image processor, and form both a photoacoustic image and an ultrasonic image has been made (see Japanese Patent Application Laid-Open (JP-A) No. 2005-21380).

SUMMARY OF THE INVENTION

JP-A No. 2005-21380 discloses a biological information processing apparatus (a subject information processing apparatus) in which the photoacoustic tomography device and the ultrasonic wave echo device are combined. In the apparatus, since a delay process is performed in an analog circuit, there is a problem in that the circuit size easily increases. Particularly, when generating photoacoustic image data, in order to perform phasing addition on a signal in real time, a plurality of reception beams inside a subject area should be processed inside a subject area. Thus, it is necessary to perform a calculation in parallel and increase a processing speed, and so the circuit size easily increases.

Further, a technique of generating both the photoacoustic image data and the ultrasonic image data in real time has not been disclosed yet. Therefore, there was a need for providing a technique capable of generating both the photoacoustic image data and the ultrasonic image data in real time and thus improving a degree of accuracy of ultrasonic diagnosis in clinical practice.

In light of the above-mentioned problems, it is an object of the present invention to provide a subject information processing apparatus in which the circuit size can be suppressed, and data of the photoacoustic tomography and the ultrasonic wave echo can be processed at a high speed.

The present invention provides a subject information processing apparatus, comprising:

an ultrasonic wave transmitter;

a light source;

a probe including a plurality of receiving elements that receive an ultrasonic wave that is transmitted from the ultrasonic wave transmitter and reflected from the inside of a subject, and a photoacoustic wave generated from the subject in reaction to an irradiation on the subject by the light source;

a plurality of memories that correspond to the plurality of receiving elements, respectively, and store signals received by the corresponding receiving elements;

a controller that performs a control to output the signals stored in the plurality of memories;

a plurality of adders that add signals output from the memories; and a processor that generates image data of the subject based on outputs from the adders, wherein the plurality of memories is divided into a plurality of groups, signals input to the plurality of adders, respectively, are configured to include only one output from the memories belonging to the same group, and the processor receives a signal obtained by adding the outputs from the plurality of adders and generates image data of the subject when processing a signal based on an ultrasonic wave, and, receives an output from each of the plurality of adders and generates image data of the subject when processing a signal based on a photoacoustic wave.

According to the subject information processing apparatus of the present invention, the circuit size can be suppressed, and data of the photoacoustic tomography and the ultrasonic wave echo can be processed at a high speed.

Further features of the present invention will become apparent from the following description of exemplary embodiments with reference to the attached drawings.

BRIEF DESCRIPTION OF THE DRAWINGS

FIG. 1B is a diagram illustrating a configuration of a reception beam forming apparatus according to the first exemplary embodiment;

DESCRIPTION OF THE EMBODIMENTS

Hereinafter, exemplary embodiments of a subject information processing apparatus will be described in detail with reference to the accompanying drawings. In the following description, a biological information processing apparatus will be described as an example of a subject information processing apparatus, but a measurement target to which the present invention can be applied is not limited thereto.

Figure 5:
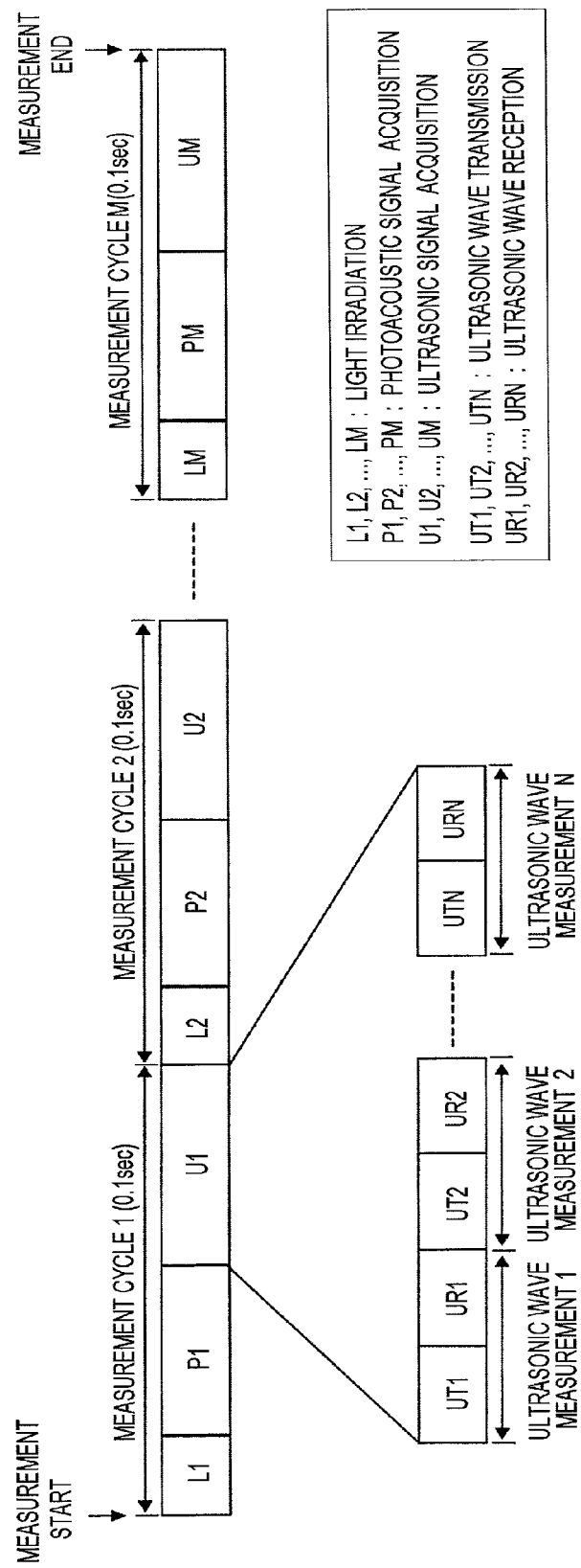
FIG. 5 is a diagram illustrating an operation sequence of a biological information processing apparatus.

First, an operation sequence of a biological information processing apparatus according to exemplary embodiments will be described with reference to FIG. 5.

Upon start of measurement, light is irradiated to a biological object in order to acquire a photoacoustic signal. Next, in a photoacoustic signal acquisition phase, a photoacoustic signal generated inside a subject area is received, and a phasing addition process is performed on all of target pixels or target voxels inside the subject area to generate photoacoustic image data. Subsequently, in an ultrasonic signal acquisition phase, an operation of transmitting an ultrasonic wave to the target pixel or the target voxel and an operation of receiving an ultrasonic wave from the target pixel or the target voxel are repetitively performed to generate ultrasonic image data. By sequentially performing the measurement cycle as described above, the photoacoustic image data and the ultrasonic image data are generated in real time.

In the case of the photoacoustic tomography, in order to avoid an excessive temperature increase in a subject tissue, a light irradiation interval is set to a predetermined time (tens of milliseconds ms) or more. That is, a long standby time is required after light irradiation. During the standby time the photoacoustic signal acquisition phase and the ultrasonic signal acquisition phase are performed. Thus, as the photoacoustic signal acquisition phase is shorter, the ultrasonic signal acquisition phase is longer, and a real time property, i.e., a frame rate of an ultrasonic image is improved. In the exemplary embodiments, by reducing the photoacoustic signal acquisition phase, the frame rate of the ultrasonic image is improved, so that the real time property does not greatly deteriorate compared to the typical ultrasonic wave echo device. Meanwhile, since the frame rate of the photoacoustic image is controlled by a light irradiation interval, the frame rate of the photoacoustic image never deteriorates as long as generation of the photoacoustic image data is finished within the light irradiation interval.

Further, within the measurement cycle, the light irradiation phase and the photoacoustic signal acquisition phase need not be necessarily performed prior to the ultrasonic signal acquisition phase. The ultrasonic signal acquisition phase may be performed prior to the light irradiation phase and the photoacoustic signal acquisition phase.

(First Exemplary Embodiment)

Figure 1A:
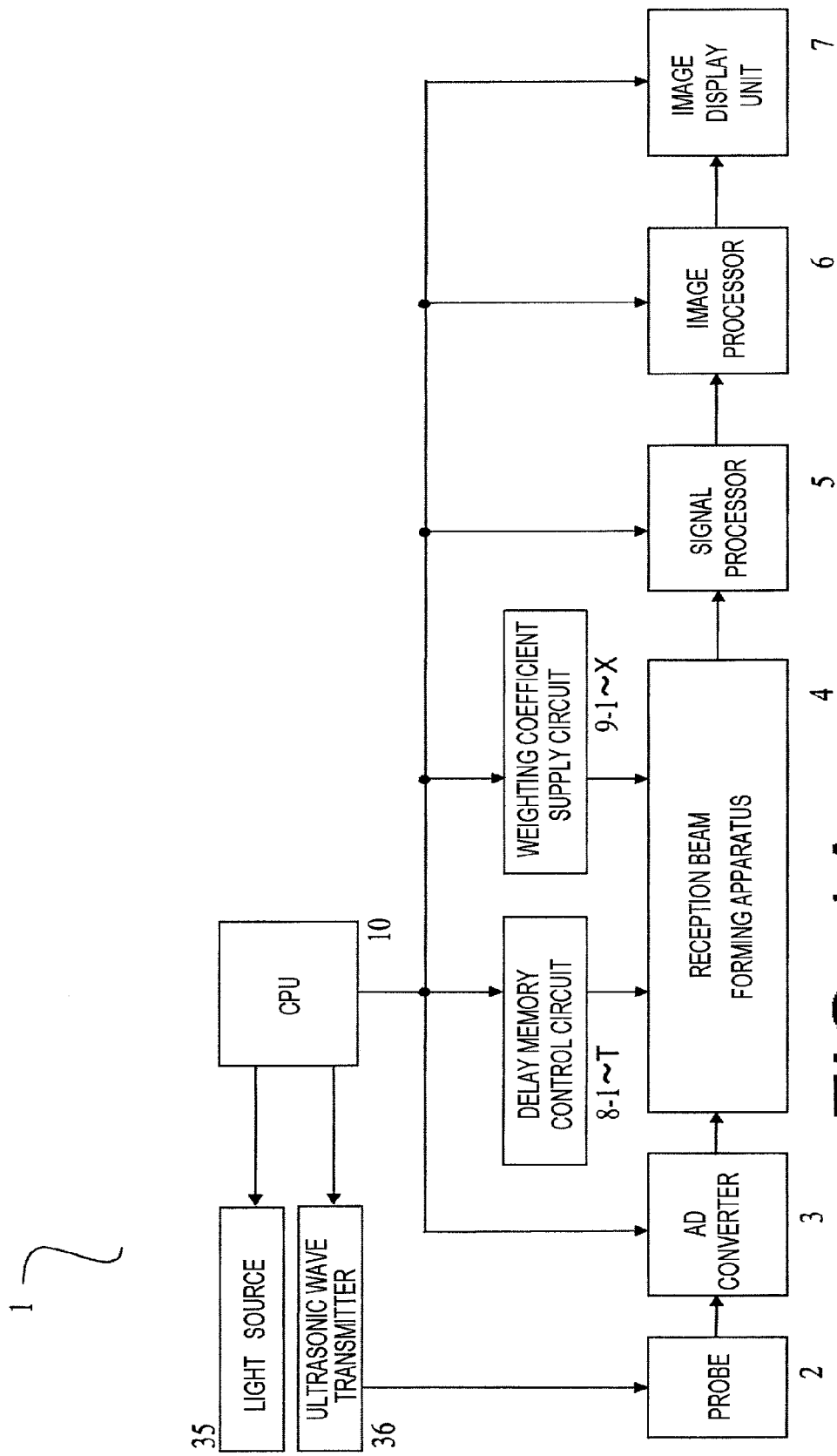
FIG. 1A is a diagram illustrating a configuration of a biological information processing apparatus according to a first exemplary embodiment.

FIG. 1A is a diagram illustrating a configuration of a biological information processing apparatus 1 according to a first exemplary embodiment.

The biological information processing apparatus 1 includes a probe 2, an analog-to-digital (AD) converter 3, a reception beam forming apparatus 4, a signal processor 5, an image processor 6, an image display unit 7, a delay memory control circuit 8, an weighting coefficient supply circuit 9, a central processing unit (CPU) 10, a light source 35, and an ultrasonic wave transmitter 36.

The light source 35 irradiates light to a subject area at certain timing under control of the CPU 10. If the light source 35 irradiates light to the subject area, a photoacoustic signal is generated inside the subject. The ultrasonic wave transmitter 36 transmits an ultrasonic wave to the subject area under control of the CPU 10. The photoacoustic signal generated inside the subject and the ultrasonic wave signal that is a reflection wave of the ultrasonic wave transmitted to the subject are received by the probe 2.

The received photoacoustic signal and the ultrasonic signal are converted into analog electrical signals by the probe 2 and then digitized by the corresponding AD converter 3. The digitalized received signal is subjected to a phasing addition process in the reception beam forming apparatus 4, and then subjected to a process such as a filtering process, a logarithmic compression process, or an envelope curve detection process in the signal processor 5. The signal processor 5 performs an appropriate process according to a property of a signal to treat. Output data of the signal processor 5 is input to the image processor 6 and subjected to a plurality of processes necessary for image data generation, so that image data is generated. The image display unit 7 displays a photoacoustic image and an ultrasonic image according to the image data generated by the image processor 6. The CPU 10 supplies data or a control signal necessary for controlling each block. The delay memory control circuits 8-1 to 8-T process delay data of the received signal, and perform reception data writing or reading control on a delay adjustment memory of the reception beam forming apparatus 4.

Here, T represents the number of delay adjustment memories disposed in the reception beam forming apparatus 4. The weight coefficient supply circuits 9-1 to 9-X process weighting data for apodization for controlling overlapping of neighboring images and supplies a weighting coefficient to a multiplier in the reception beam forming apparatus 4. Further, X represents the number of multipliers for apodization disposed in the reception beaming forming apparatus 4. The delay memory control circuit 8 corresponds to a controller, and the signal processor 5 and the image processor 6 correspond to a processor.

FIG. 1B is a diagram illustrating the reception beam forming apparatus 4 and a peripheral circuit thereof according to the first exemplary embodiment.

The reception beam forming apparatus 4 includes a delay adjustment memory 11, a multiplier 12, an adder sub block 13, and a total adder circuit 14.

The received signal digitalized by the AD converter 3 is input to the corresponding delay adjustment memory 11. The delay memory control circuit 8 supplies the delay adjustment memory 11 with a delay adjustment memory address in which the received digital data derived from the target pixel or the target voxel is stored based on target pixel or target voxel coordinates inside the subject area. The received digital data derived from the target pixel or the target voxel inside the subject area is read out from the delay adjustment memory 11 according to the delay adjustment memory address output from the delay memory control circuit 8. The received digital data is output to the multiplier 12, in the reception beam forming apparatus 4, corresponding to the delay adjustment memory 11.

A read location control block 15 and a delay table 16 are components of the delay memory control circuit 8. The delay table 16 stores delay information supplied from the CPU 10. The read location control block 15 computes the delay adjustment memory address based on the delay information stored in the delay table 16 and supplies each delay adjustment memory 11 with the delay adjustment memory address.

Figure 1C:
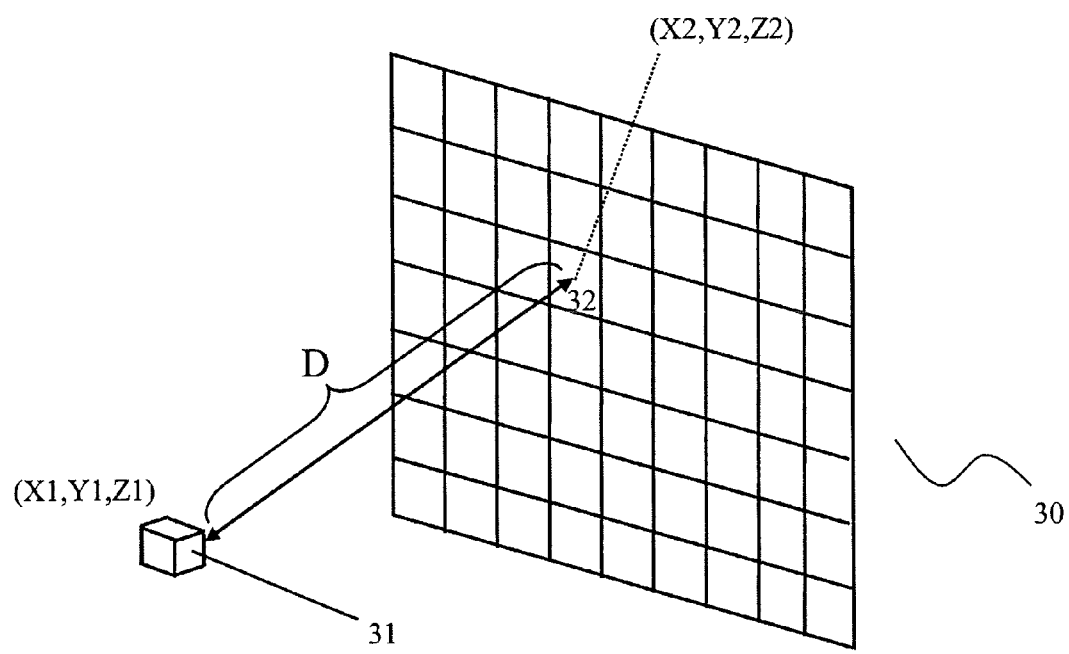
FIG. 1C is a diagram illustrating a phasing addition process of a biological information processing apparatus.

FIG. 1C illustrates an example of a position relationship among a target pixel or target voxel 31 inside the target subject area, the receiving element array 30, and the receiving element 32 in the array. If coordinates (X1, Y1, Z1) of the target pixel or voxel 31 and coordinates (X2, Y2, Z2) of the receiving element 32 are decided under a predetermined coordinate system, a distance D between the target pixel or voxel 31 and the receiving element 32 is obtained by the theorem of three squares. By dividing the distance D between the target pixel or voxel 31 and the receiving element 32 in the array by the velocity of sound, a photoacoustic wave arrival time from the target pixel or target voxel 31 to the receiving element 32 in the array is calculated.

While the photoacoustic signal or the ultrasonic signal is received from the inside of the target subject area, the delay adjustment memory 11 sequentially stores digital data derived from the photoacoustic signal or the ultrasonic signal at each memory address in time series according to a certain rule.

Thus, a relationship between the photoacoustic wave arrival time from the target pixel or target voxel 31 to the receiving element 32 in the array and the digital data storage rule in the delay adjustment memory 11 becomes clear. The delay adjustment memory address at which the digital data derived from the target pixel or target voxel is stored can be specified based on the relationship. The delay memory control circuit 8 supplies the delay adjustment memory 11 with the delay adjustment memory address. The delay adjustment memory 11 outputs the digital data derived from the target pixel or target voxel 31 to the multiplier 12 according to the delay adjustment memory address allocated from the delay memory control circuit 8.

The weighting coefficient supply circuit 9 supplies the multiplier 12 with a window function weighting coefficient optimal to the target pixel or target voxel based on the coordinates of the target pixel or target voxel inside the subject area. The digital data, output from the delay adjustment memory 11, with the window function weighting coefficient calculated by the weighting coefficient supply circuit 9 for each channel for apodization is output to the adder sub block 13. The adder sub block 13 is an adder. The adder sub block 13 divides the digital data with the window function weighting coefficient into a plurality of adding groups and adds only the received digital data belonging to each adding group. The total adder circuit 14 is an adder and adds all of outputs of the adder sub blocks 13-1 to 13-3.

Here, a difference between a technique of receiving the ultrasonic signal and a technique of receiving the photoacoustic signal will be described. At the time of transmission of the ultrasonic wave, by transmitting the ultrasonic wave to which the delay time corresponding to the distance between the target pixel or voxel and each receiving element is added, the transmission beam can be converged. By adding all of signals that are reflected from the target pixel or voxel and detected by the receiving elements, the signal strength can be obtained. Therefore, at the time of reception of the ultrasonic signal, an output of the total adder circuit 14 is transmitted to the signal processor 5 as phasing addition data.

Meanwhile, in the photoacoustic tomography, since it is difficult to converge light at an arbitrary place due to influence of scattering inside the subject, a parallel process is performed for each of one time light irradiation. Therefore, at the time of reception of the photoacoustic signal, the outputs of the adder sub blocks 13-1 to 13-3 are transmitted to the signal processor 5 as the phasing addition data.

Subsequently, an adding group division method in the adder sub blocks 13-1 to 13-3 will be described. In a field of the ultrasonic wave echo device, it has generally been known that in order not to generate aside lobe at the time of reception beam formation by the phasing addition, a receiving element pitch is preferably equal to or less than half (½) of a wavelength of a received signal. In the case of the photoacoustic tomography device, the frequency of the photoacoustic signal that is generated by irradiating light to a human body and then arrives at the receiving element is about 1 MHz. Meanwhile, in the ultrasonic wave echo device, the frequency of the ultrasonic signal may be more than 10 MHz. For example, let us assume that a probe having an intermediate frequency band of 6 MHz is used. In this case, the intermediate frequency of the photoacoustic signal is 1 MHz, whereas the intermediate frequency of the ultrasonic signal is 6 MHz, so that a wavelength difference of 6 times occurs. That is, on the photoacoustic signal, the receiving element pitch of the 6 MHz probe for the ultrasonic signal becomes finer more than necessary.

Therefore, in the first exemplary embodiment, at the time of acquisition of the photoacoustic signal, a plurality of neighboring receiving elements are collectively considered as one element, and the receiving element pitch effectively increases. For example, referring to FIG. 1B, the three neighboring receiving elements are combined as one group, and one group is collectively considered as one element. In this case, the AD converters 3-1 to 3-3 connected to the three neighboring receiving elements belonging to the same group are considered as if they are connected to one element in parallel. Further, it is considered that the same reception data is stored in the delay adjustment memories 11-1 to 11-3, respectively. Similarly, the AD converters 3-4 to 3-6 and the AD converters 3-7 to 3-9 are also considered as if they are connected to one element in parallel. Further, it is considered that the same reception data is stored in the delay adjustment memories 11-4 to 11-6 and the delay adjustment memories 11-7 to 11-9, respectively.

In this configuration, three circuits each of which includes the AD converter 3, the delay adjustment memory 11, and the multiplier 12 are connected to one adding group (substantially considered as one element) in parallel. Therefore, the adder sub block 13-1 is connected to the multipliers 12-1, 12-4, and 12-7, the adder sub block 13-2 is connected to the multipliers 12-2, 12-5, and 12-8, and the adder sub block 13-3 is connected to the multipliers 12-3, 12-6, and 12-9. If the outputs of the adder sub blocks 13-1 to 13-3 can be acquired, respectively, the same configuration as three phasing addition circuits are disposed in parallel is made. At this time, the outputs from the delay adjustment memories belonging to the same adding group are input to the adder sub blocks, respectively, without overlapping. As a result, in the example of FIG. 1B, at the time of reception of the photoacoustic signal, the phasing addition processing ability that is three times as high as at the time of reception of the ultrasonic signal is obtained.

Further, the number of receiving elements combined as one group is not necessarily three. The number of receiving elements combined as one group may be decided according to a degree of adjacency between the receiving elements to the extent that the side lobe does not occur.

Further, a value obtained by adding the outputs of a plurality of AD converters 3 connected to the receiving elements substantially considered as one element may be input to the delay adjustment memory 11. For example, an adding result obtained by adding the outputs of the AD converters 3-1 to 3-3 is input to the delay adjustment memories 11-1 to 11-3. Similarly, an adding result obtained by adding the outputs of the AD converters 3-4 to 3-6 is input to the delay adjustment memories 11-4 to 11-6. Further, similarly, an adding result obtained by adding the outputs of the AD converters 3-7 to 3-9 is input to the delay adjustment memories 11-7 to 11-9. By this configuration, the received signals input to the three AD converters 3 overlap, so that a signal to noise ratio (SNR) of the received photoacoustic signal is improved.

Further, only one reception beam forming apparatus 4 is not necessarily disposed. If allowed from a point of view of a system scale, a plurality of reception beam forming apparatuses 4 may be disposed in parallel, leading to a configuration of further increasing the phasing addition processing ability.

According to the first exemplary embodiment, it is possible to process both the photoacoustic signal and the ultrasonic signal even while commonalizing the circuits of the photoacoustic tomography device and the ultrasonic wave echo device.

In addition, according to the first exemplary embodiment, at the time of acquisition of the photoacoustic signal, the same effect as a plurality of phasing addition circuits are disposed in parallel can be obtained, and thus the phasing addition process of the photoacoustic signal can be performed at a high speed. Therefore, both the photoacoustic image data and the ultrasonic image data can be generated in real time without remarkably deteriorating the frame rate of the ultrasonic image. Further, the SNR of the received photoacoustic signal can be improved.

(Second Exemplary Embodiment)

Figure 2A:
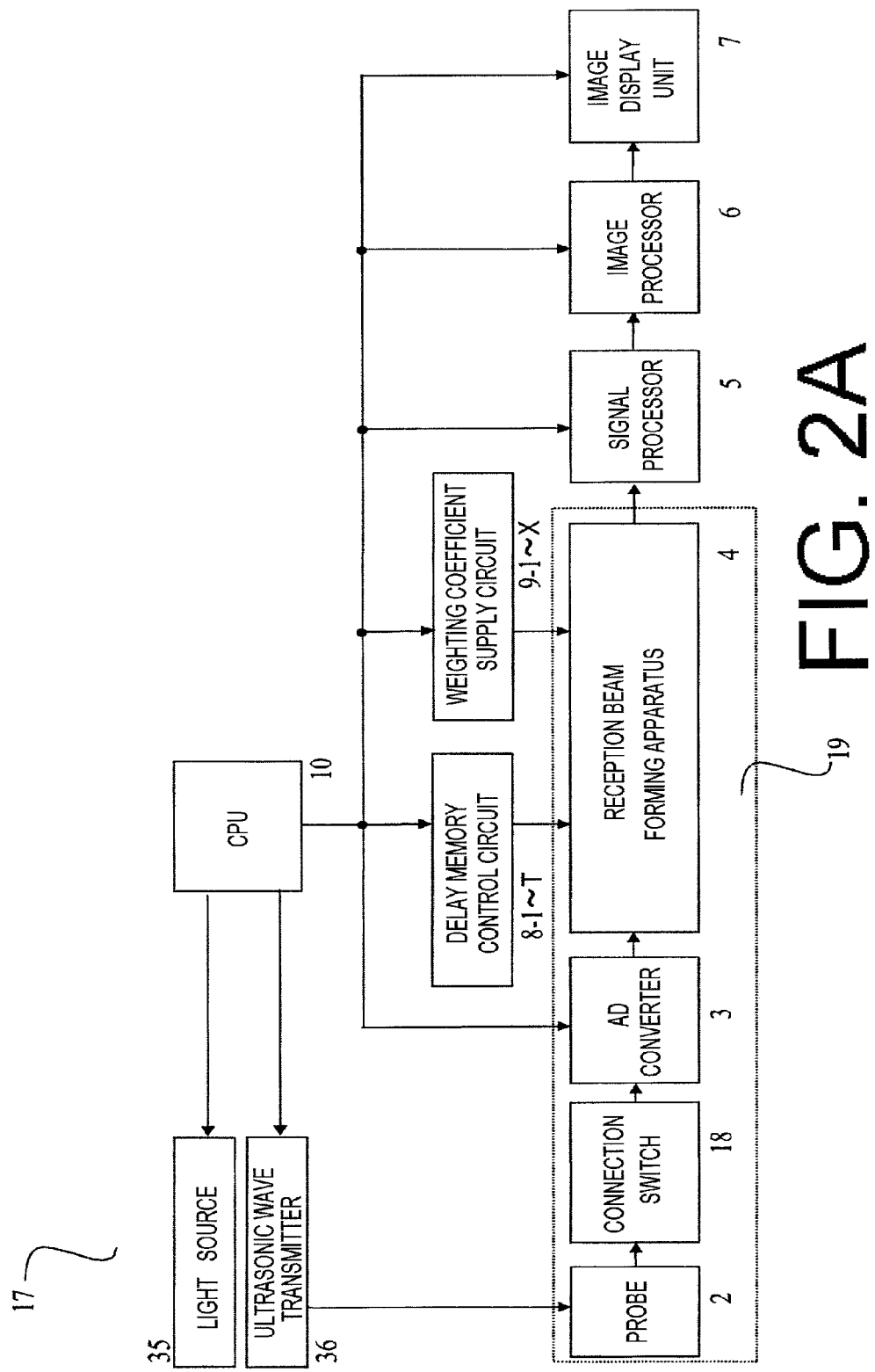
FIG. 2A is a diagram illustrating a configuration of a biological information processing apparatus according to a second exemplary embodiment.

FIG. 2A is a diagram illustrating a configuration of a biological information processing apparatus 17 according to a second exemplary embodiment. The biological information processing apparatus 17 has the same configuration as in the first exemplary embodiment except that a connection switch 18 is connected between the probe 2 and the AD converter 3.

The connection switch 18 functions to switch a connection state between the receiving element of the probe 2, and the AD converter 3 and the delay adjustment memory 11.

Figure 2B:
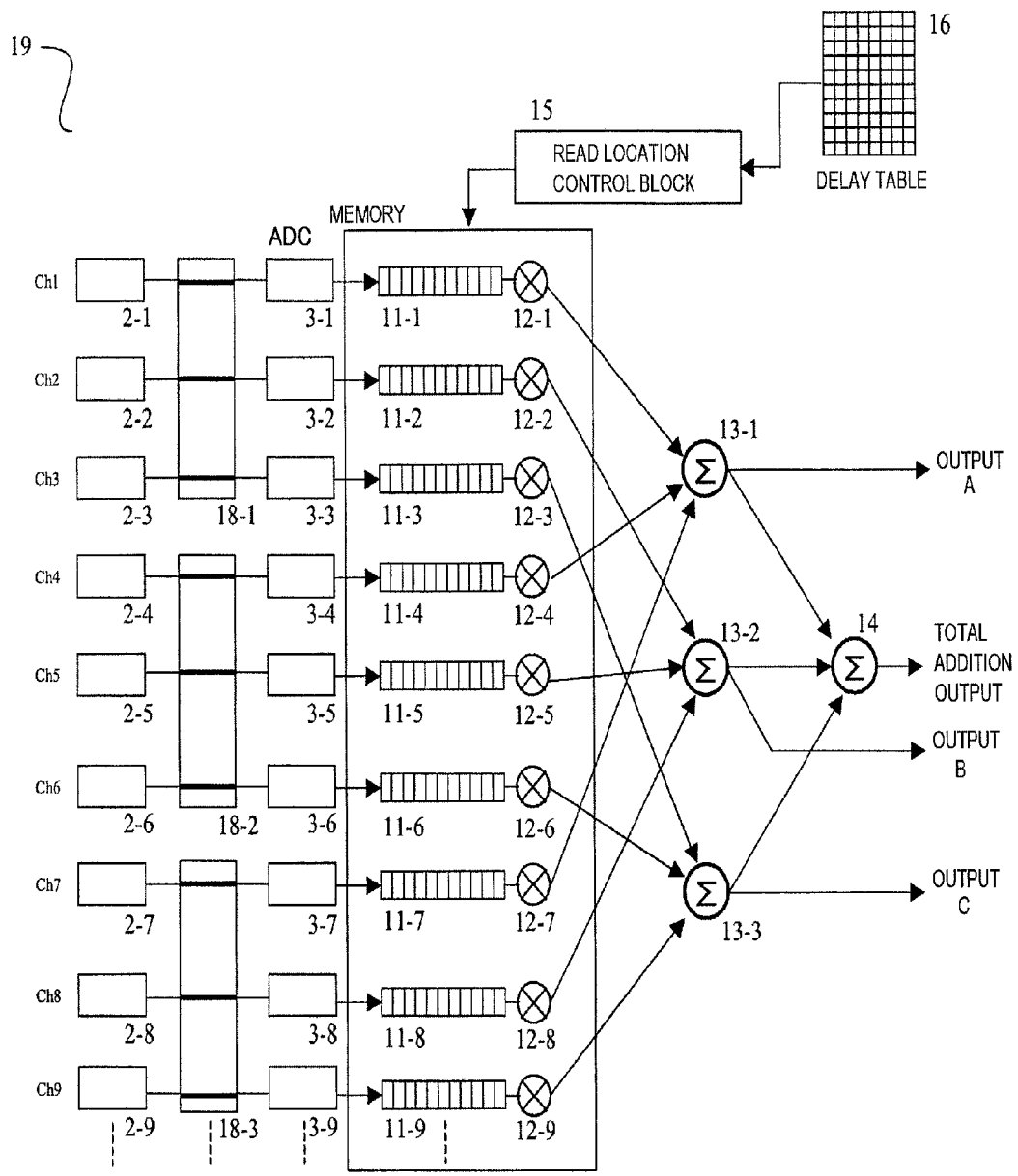
FIG. 2B is a diagram illustrating an operation example of a reception beam forming apparatus according to the second exemplary embodiment.

FIG. 2B is a diagram illustrating a reception beam forming apparatus 4 and a peripheral circuit thereof at the time of acquisition of the ultrasonic signal according to the second exemplary embodiment.

In the second exemplary embodiment, the connection state of the connection switch 18 is switched between the time of acquisition of the photoacoustic signal and the time of acquisition of the ultrasonic signal. At the time of acquisition of the ultrasonic signal, as illustrated in FIG. 2B, the receiving elements 2-1 to 2-9 are individually connected to the AD converters 3-1 to 3-9. The ultrasonic signal data received in the receiving elements 2-1 to 2-9 are digitalized in the AD converters 3-1 to 3-9 and stored in the delay adjustment memories 11-1 to 11-9, respectively. The digital data stored in the delay adjustment memories 11-1 to 11-9 are read out according to the delay adjustment memory address supplied from the delay memory control circuits 8-1 to 8-9, respectively. The read digital data is subjected to the adding process in the adder sub blocks 13-1 to 13-3 and the total adder circuit 14 and then transmitted to the signal processor 5 as the phasing addition data.

Figure 2C:
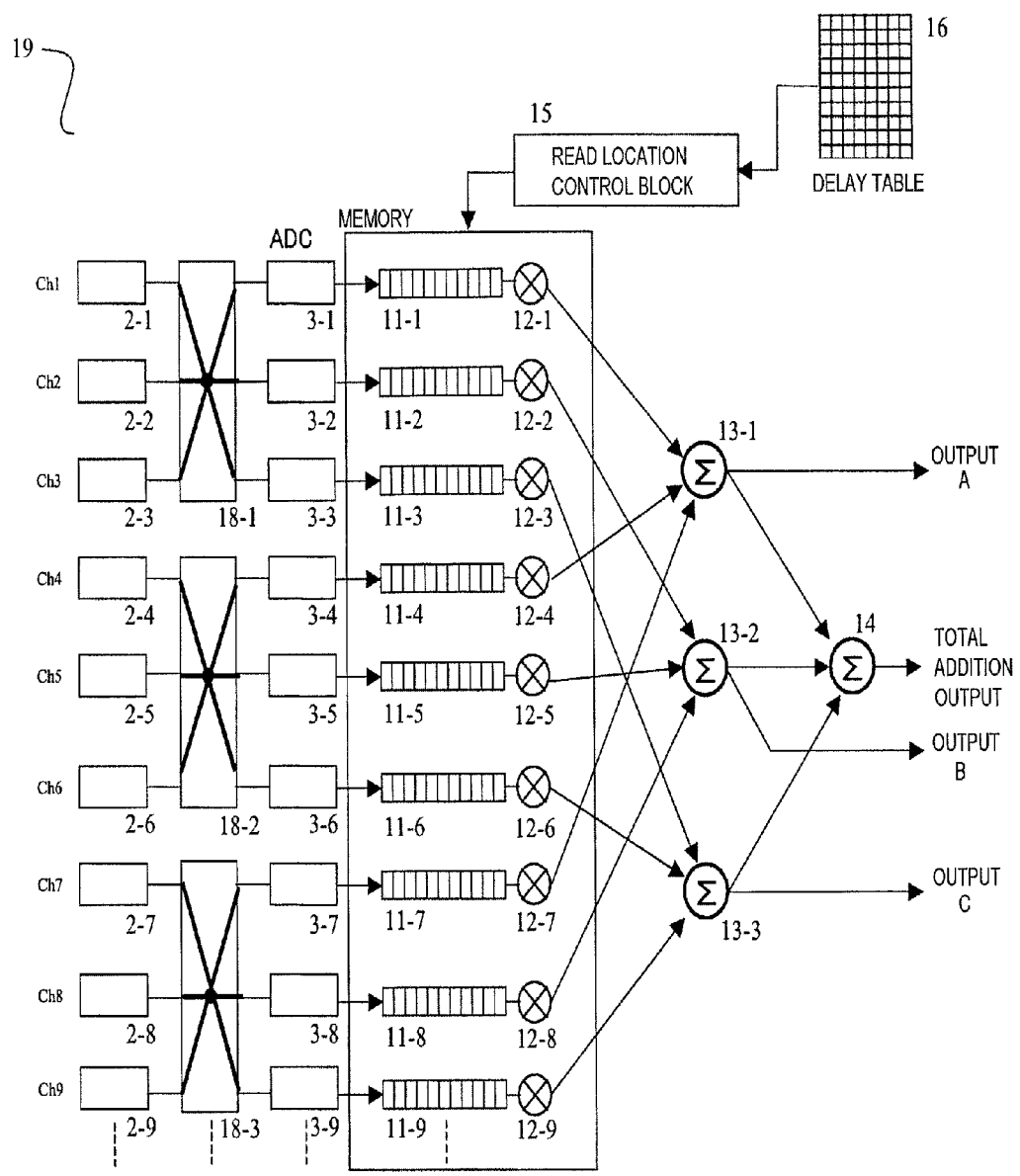
FIG. 2C is a diagram illustrating an operation example of a reception beam forming apparatus according to the second exemplary embodiment.

FIG. 2C is a diagram illustrating the reception beam forming apparatus 4 and the peripheral circuit thereof at the time of acquisition of the photoacoustic signal according to the second exemplary embodiment. In this case, the receiving elements 2-1 to 2-3 are coupled by the connection switch 18-1 and then connected to the AD converters 3-1 to 3-3. Similarly, the receiving elements 2-4 to 2-6 are coupled by the connection switch 18-2 and then connected to the AD converters 3-4 to 3-6. Further, the receiving elements 2-7 to 2-9 are coupled by the connection switch 18-3 and then connected to the AD converters 3-7 to 3-9. Through the above configuration, the three neighboring receiving elements are combined as one group, and one group is collectively considered as one element. In this case, the AD converters 3-1 to 3-3 connected to the three neighboring receiving elements are considered as if they are connected to one element in parallel. The same reception data is stored in the delay adjustment memories 11-1 to 11-3, respectively. This can be similarly applied to the AD converters 3-4 to 3-6, the AD converters 3-7 to 3-9, the delay adjustment memories 11-4 to 11-6, and the delay adjustment memories 11-7 to 11-9.

In the second exemplary embodiment, at the time of reception of the photoacoustic signal, the phasing addition processing ability that is three times as high as at the time of reception of the ultrasonic signal is obtained as in the first exemplary embodiment. Further, since the received signals of the plurality of neighboring receiving elements overlap, there is an effect capable of improving the SNR of the received signal input to the AD converter 3.

Further, the number of receiving elements combined as one group is not necessarily three. A number of receiving elements may be combined to the extent that the side lobe does not occur even if the elements are combined.

Further, the connection switch 18 may be disposed at the apparatus body side or built in at the probe side.

According to the second exemplary embodiment, it is possible to process both the photoacoustic signal and the ultrasonic signal even while commonalizing the circuits of the photoacoustic tomography device and the ultrasonic wave echo device. At the time of acquisition of the photoacoustic signal, the same effect as a plurality of phasing addition circuits are disposed in parallel can be obtained, and thus the phasing addition process of the photoacoustic signal can be performed at a high speed. Therefore, both the photoacoustic image data and the ultrasonic image data can be generated in real time without remarkably deteriorating the frame rate of the ultrasonic image.

Further, at the time of reception of the photoacoustic signal, the SNR of the received photoacoustic signal can be improved by overlapping the received signals.

(Third Exemplary Embodiment)

Figure 3:
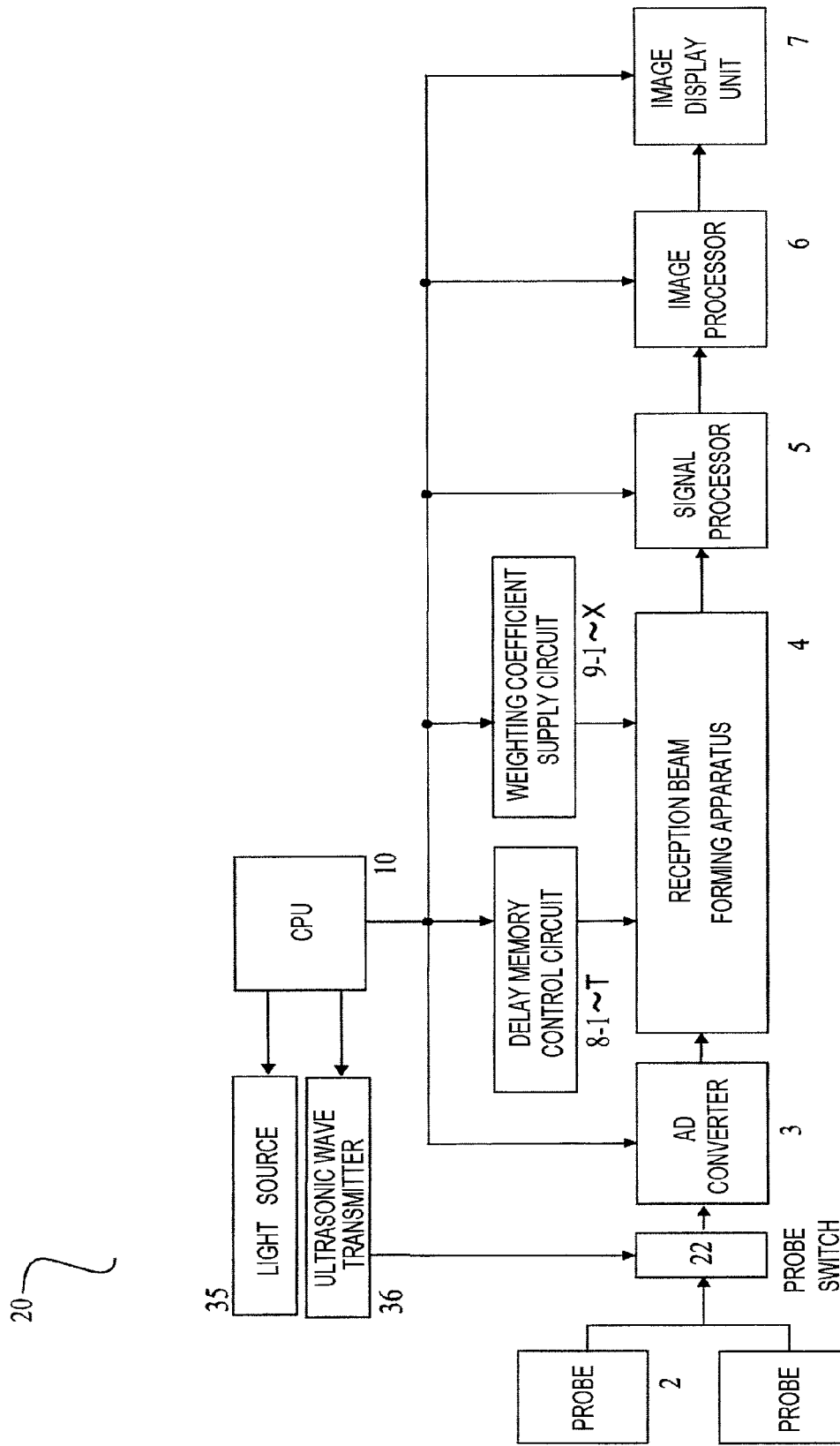
FIG. 3 is a diagram illustrating a configuration of a biological information processing apparatus according to a third exemplary embodiment.

FIG. 3 is a diagram illustrating a configuration of a biological information processing apparatus 20 according to a third exemplary embodiment.

The biological information processing apparatus 20 has the same configuration as in the first exemplary embodiment except that a probe switch 22 is disposed between the probe and the AD converter 3 and between the probe and the ultrasonic wave transmitter 36, and a probe 21 is added.

The probe switch 22 functions to switch a connection state between the AD converter 3 and the probes 2 and 21. For example, let us assume that a 1 MHz probe suitable for acquisition of the photoacoustic signal is used as the probe 2, and a 6 MHz probe used for typical ultrasonic diagnosis is used as the probe 21. The probe switch 22 may operate such that at the time of acquisition of the photoacoustic signal, the probe 2 is connected to the AD converter 3, and at the time of acquisition of the ultrasonic signal, the probe 21 is connected to the AD converter 3. The receiving element of the probe 21 corresponds to an ultrasonic wave receiving element, and the receiving element of the probe 2 corresponds to a photoacoustic wave receiving element.

The number of probes switched by the probe switch 22 is not necessary limited to two and may arbitrarily change according to a need. Further, a kind of the probe that is a switching target is not limited to one which uses general piezoelectric ceramics and may be replaced with, for example, a capacitance type ultrasonic transducer adapting a semiconductor process.

According to the third exemplary embodiment, it is possible to process both the photoacoustic signal and the ultrasonic signal even while commonalizing the circuits of the photoacoustic tomography device and the ultrasonic wave echo device.

Further, at the time of acquisition of the photoacoustic signal, the same effect as a plurality of phasing addition circuits are disposed in parallel can be obtained, and thus the phasing addition process of the photoacoustic signal can be performed at a high speed. Therefore, both the photoacoustic image data and the ultrasonic image data can be generated in real time without remarkably deteriorating the frame rate of the ultrasonic image. Further, the SNR of the received photoacoustic signal can be improved.

Further, according to the third exemplary embodiment, the photoacoustic signal and the ultrasonic signal that are greatly different in intermediate frequency can be processed by a single signal processing system by using a plurality of probes having different characteristics.

(Fourth Exemplary Embodiment)

Figure 4:
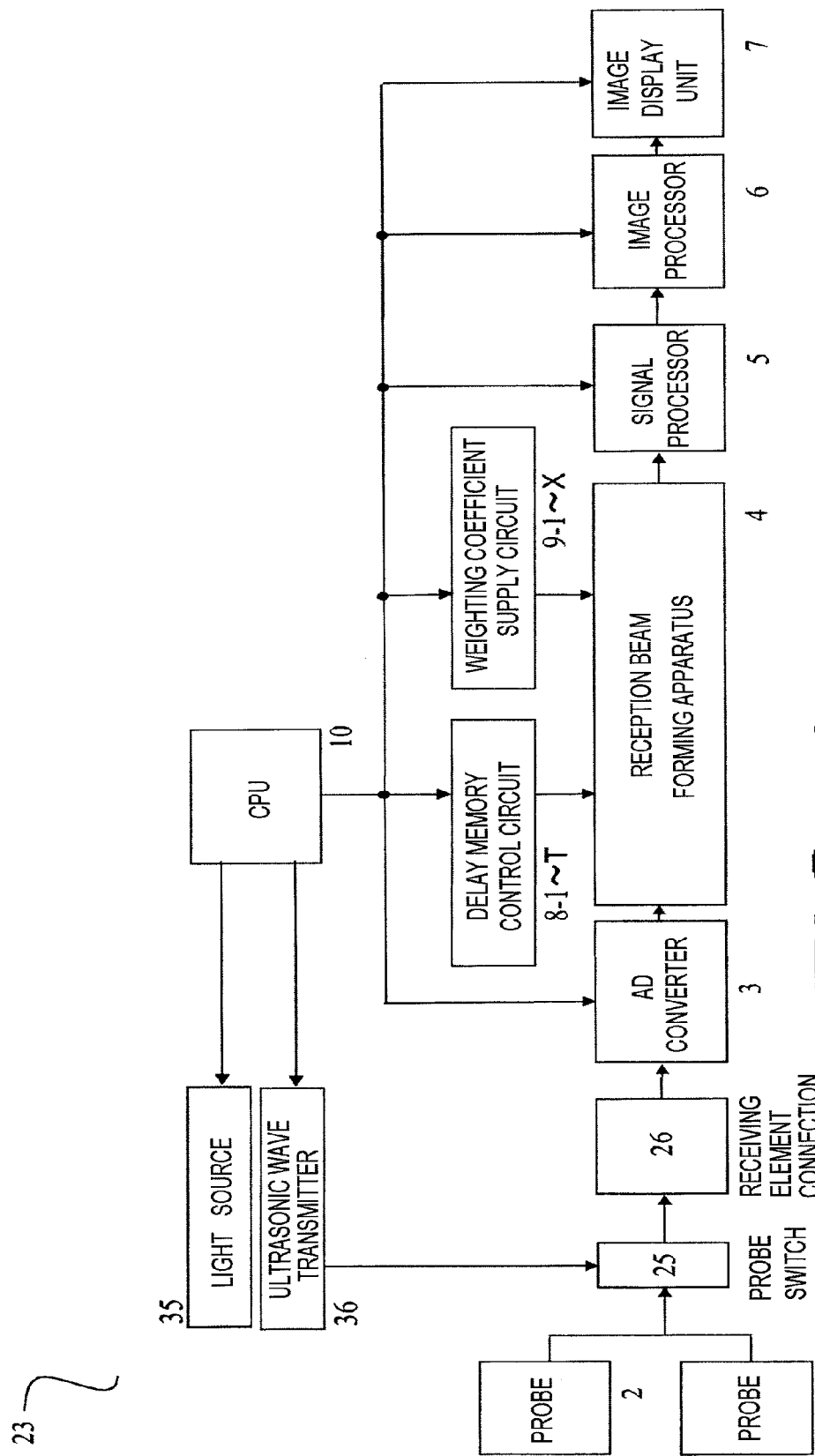
FIG. 4 is a diagram illustrating a configuration of a biological information processing apparatus according to a fourth exemplary embodiment.

FIG. 4 is a diagram illustrating a configuration of a biological information processing apparatus 23 according to a fourth exemplary embodiment.

The biological information processing apparatus 23 has the same configuration as in the first exemplary embodiment except that a probe 24, a probe switch 25, and a receiving element connection switch 26 are added. The probe switch 25 is disposed between the probe and the receiving element connection switch 26 and between the probe and the ultrasonic wave transmitter 36. The receiving element connection switch 26 is disposed between the probe switch 25 and the AD converter 3.

The probe switch 25 functions to switch a connection state between the AD converter 3 and the probes 2 and 24 and has the same function as the probe switch of the third exemplary embodiment. For example, let us assume that a 1 MHz probe suitable for acquisition of the photoacoustic signal is used as the probe 2, and a 6 MHz probe used for typical ultrasonic diagnosis is used as the probe 24. The probe switch 25 may operate such that at the time of acquisition of the photoacoustic signal, the probe 2 is connected to the AD converter 3, and at the time of acquisition of the ultrasonic signal, the probe 24 is connected to the AD converter 3.

The receiving element connection switch 26 performs a process of switching a connection between the probe and the AD converter so that a plurality of outputs from the receiving elements of the probe 2 for receiving the photoacoustic signal can be collectively input to the AD converter 3. At this time, for example, the outputs from the three neighboring receiving elements are input to the AD converter. When the probe switch 25 performs switching to the probe 2 to receive the photoacoustic signal, the receiving element connection switch 26 combines the outputs of the receiving elements of the probe 2. Therefore, since the signals from the plurality of receiving elements overlap, the SNR can be improved.

The number of probes switched by the probe switch 25 is not necessary limited to two and may arbitrarily change according to a need. Further, a kind of the probe that is a switching target is not limited to one which uses general piezoelectric ceramics as a material and may be replaced with, for example, a capacitance type ultrasonic transducer adapting a semiconductor process.

According to the fourth exemplary embodiment, it is possible to process both the photoacoustic signal and the ultrasonic signal even while commonalizing the circuits of the photoacoustic tomography device and the ultrasonic wave echo device.

Further, at the time of acquisition of the photoacoustic signal, the same effect as a plurality of phasing addition circuits are disposed in parallel can be obtained, and thus the phasing addition process of the photoacoustic signal can be performed at a high speed. Therefore, both the photoacoustic image data and the ultrasonic image data can be generated in real time without remarkably deteriorating the frame rate of the ultrasonic image. Further, the SNR of the received photoacoustic signal can be improved.

Further, according to the fourth exemplary embodiment, the photoacoustic signal and the ultrasonic signal that are greatly different in intermediate frequency can be processed by a single signal processing system by using a plurality of probes having different characteristics. At this time, the SNR of the photoacoustic signal can be improved by coupling the plurality of receiving elements.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-037024, filed on Feb. 23, 2010, which is hereby incorporated by reference herein in its entirety.

What is claimed is:

1. A subject information processing apparatus, comprising:
    an ultrasonic wave transmitter;
    a light source;
    a plurality of receiving elements that receive an ultrasonic wave that is transmitted from said ultrasonic wave transmitter and reflected from inside a subject, and a photoacoustic wave generated from the subject in reaction to irradiation of the subject by said light source;
    a plurality of analog-to-digital converters that convert signals output from said receiving elements to digital signals respectively;
    a plurality of memories that store the digital signals in time series output from said analog-digital converters;
    a controller that reads out, with respect to each target in the subject, the digital signal corresponding to the position of the target from said plurality of memories;
    a plurality of first adders that are electrically connected to said plurality of analog-to-digital converters through said plurality of memories and add digital signals read out from said plurality of memories;
    a second adder that add signals output from said plurality of first adders; and
    a processor that generates image data of the subject,
    wherein said memories are grouped into a plurality of groups, each group includes memories corresponding to a predetermined number of contiguous elements, from among said plurality of memories, and memories in the same group are electrically connected to different ones of said first adders respectively,
    and
    wherein said processor generates image data of the subject by using an output from said second adder in a case of processing signals derived from ultrasonic waves, and generates image data of the subject by using an output from each of said plurality of first adders in a case of processing signals derived from photoacoustic waves.

2. The subject information processing apparatus according to claim 1, wherein, in a case in which said memories store the digital signals derived from photoacoustic waves, a digital signal from one of said receiving elements is also input to another memory belonging to the same group.

3. The subject information processing apparatus according to claim 1, wherein said plurality of receiving elements serve as said ultrasonic wave transmitter.

4. The subject information processing apparatus according to claim 1,
wherein said plurality of elements includes a plurality of elements for receiving the ultrasonic wave and a plurality of elements for receiving the photoacoustic wave;
wherein transmission of the ultrasonic wave by said ultrasonic wave transmitter and reception of the ultrasonic wave by said plurality of elements for receiving the ultrasonic wave, and light irradiation by said light source and reception of the photoacoustic wave by said plurality of elements for receiving the photoacoustic wave are sequentially performed, and
wherein the subject information processing apparatus further comprises a switch that switches said elements such that in a phase of receiving the ultrasonic wave, said elements for receiving the ultrasonic wave are used, and in a phase of receiving the photoacoustic wave, said elements for receiving the photoacoustic wave are used.

5. A subject information processing apparatus, comprising:
a plurality of receiving elements that receive a first ultrasonic wave having a first intermediate frequency propagated from inside a subject, and a second ultrasonic wave having a second intermediate frequency which is lower than the first intermediate frequency and propagated from the subject;
a plurality of analog-to-digital converters that convert signals output from said receiving elements to digital signals respectively,
a plurality of memories that store the digital signals in time series output from said analog-digital converters;
a controller that reads out, with respect to each target in the subject, the digital signal corresponding to the position of the target from said plurality of memories;
a plurality of first adders that are electrically connected to said plurality of analog-to-digital converters through said plurality of memories and add digital signals read out from said plurality of memories;
a second adder that adds signals output from said plurality of first adders; and
a processor that generates image data of the
wherein said plurality of memories are grouped into a plurality of groups, each group includes memories corresponding to a predetermined number of contiguous ones of said elements, from among the plurality of memories, and memories in the same group are electrically connected to different ones of said first adders respectively,
and
wherein the processor generates image data of the subject by using an output from said second adder in a case of processing signals derived from first ultrasonic waves, and generates image data of the subject by using an output from each of said plurality of first adders and in a case of processing signals derived from second ultrasonic waves.

6. The subject information processing apparatus according to claim 5, wherein, in a case in which said memories store the digital signals derived from second ultrasonic waves, a digital signal from one of said receiving elements is also input to another memory belonging to the same group.

7. The subject information processing apparatus according to claim 5, wherein said plurality of receiving elements serve as said ultrasonic wave transmitter.

8. The subject information processing apparatus according to claim 5, further comprising:
an ultrasonic wave transmitter that transmits the first ultrasonic wave; and
a light source,
wherein the first ultrasonic wave is transmitted from said ultrasonic wave transmitter and reflected and propagated from inside the subject,
wherein the second ultrasonic wave is generated and propagated from the subject in reaction to irradiation of the subject by said light source,
wherein said plurality of elements includes a plurality of elements for receiving the first ultrasonic wave and a plurality of elements for receiving the second ultrasonic wave,
wherein transmission of the first ultrasonic wave by said ultrasonic wave transmitter and reception of the first ultrasonic wave by said plurality of elements for receiving the first ultrasonic wave, and light irradiation by said light source and reception of the second ultrasonic wave by said plurality of elements for receiving the second ultrasonic wave are sequentially performed, and
wherein the subject information processing apparatus further comprises a switch that switches said elements such that in a phase of receiving the first ultrasonic wave, said elements for receiving the first ultrasonic wave are used, and in a phase of receiving the second ultrasonic wave, said elements for receiving the second ultrasonic wave are used.

* * * * *